United States Patent [19]

Khuri-Yakub

[11] Patent Number: 4,620,443
[45] Date of Patent: Nov. 4, 1986

[54] LOW FREQUENCY ACOUSTIC MICROSCOPE

[75] Inventor: Butrus T. Khuri-Yakub, Palo Alto, Calif.

[73] Assignee: The Board of Trustees of The Leland Stanford Junior University, Stanford, Calif.

[21] Appl. No.: 681,229

[22] Filed: Dec. 13, 1984

[51] Int. Cl.⁴ .............................................. G01N 29/04
[52] U.S. Cl. ........................................................ 73/606
[58] Field of Search .................. 73/606, 607, 620, 629

[56] References Cited

U.S. PATENT DOCUMENTS 4,394,824  7/1983  Kanda et al. ........................... 73/606
4,524,621  6/1985  Yamanaka ............................... 73/606

FOREIGN PATENT DOCUMENTS 0129354  8/1983  Japan .

OTHER PUBLICATIONS

R. D. Weglein, "A Model for Predicting Acoustic Material Signatures" Appl. Phys. Lett. 34 (3), pp. 179–181, Feb. 1979.

*Primary Examiner*—Stephen A. Kreitman
*Attorney, Agent, or Firm*—Flehr, Hohbach, Test, Albritton & Herbert

[57] ABSTRACT

A scanning acoustic microscope is disclosed for the detection and location of near surface flaws, inclusions or voids in a solid sample material. A focused beam of acoustic energy is directed at the sample with its focal plane at the subsurface flaw, inclusion or void location. The sample is scanned with the beam. Detected acoustic energy specularly reflected and mode converted at the surface of the sample and acoustic energy reflected by subsurface flaws, inclusions or voids at the focal plane are used for generating an interference signal which is processed and forms a signal indicative of the subsurface flaws, inclusions or voids.

4 Claims, 3 Drawing Figures

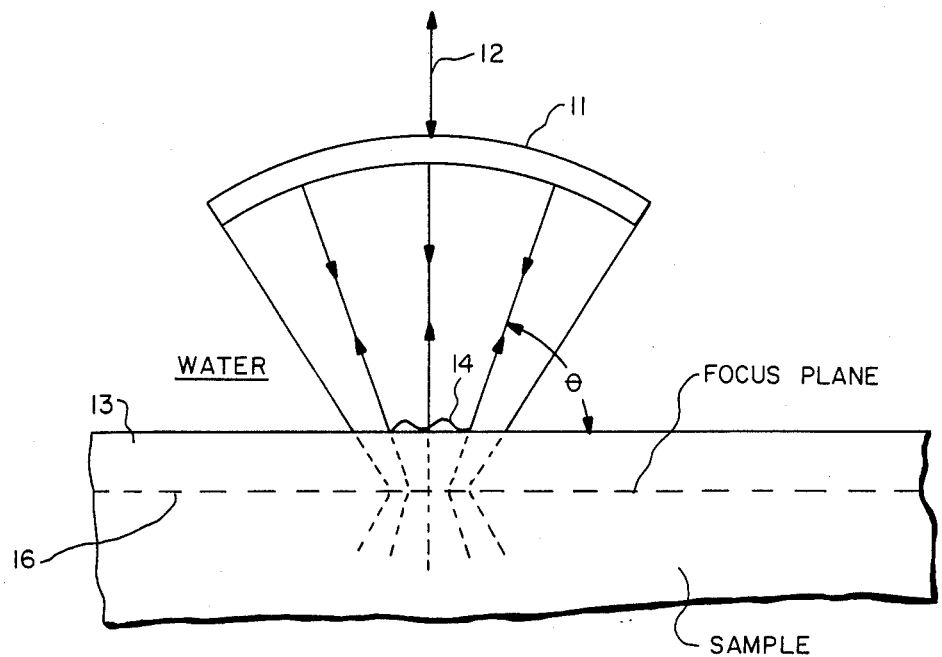
FIG.—1
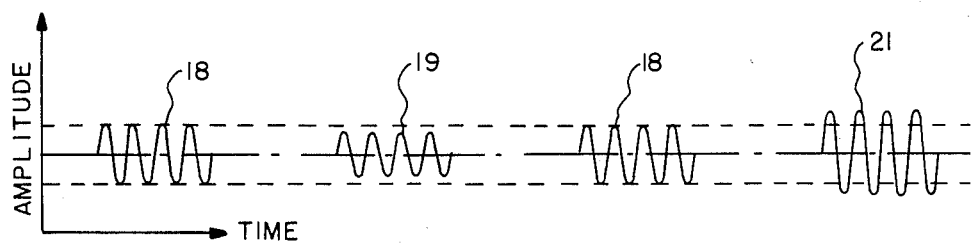
FIG.—2

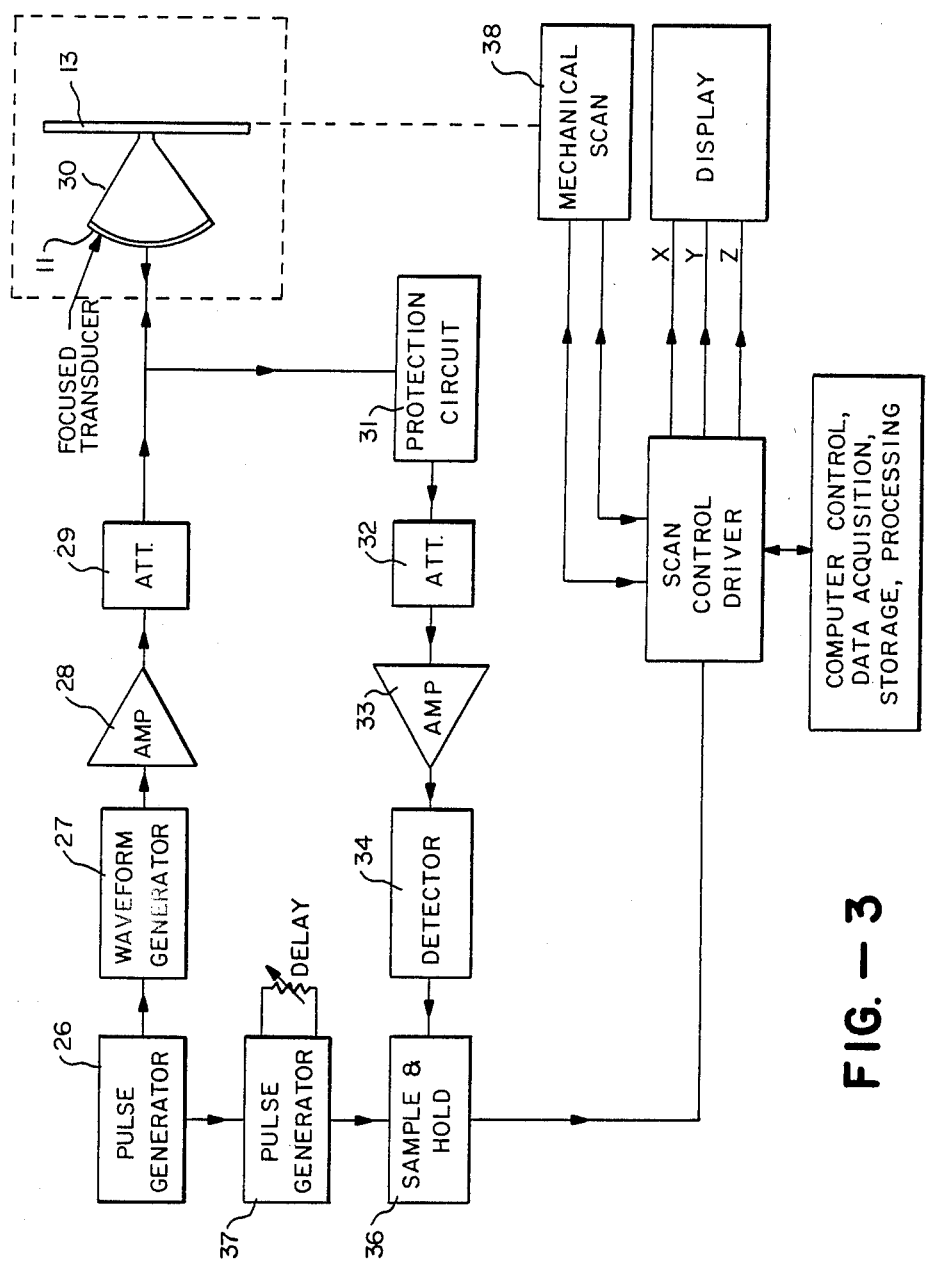
FIG. —3

LOW FREQUENCY ACOUSTIC MICROSCOPE

This invention relates generally to scanning acoustic microscope and method, and more particularly to an acoustic microscope for the detection and the location of near surface flaws, inclusions or voids in a solid sample material.

Scanning acoustic microscopes are well known. Basically, the prior art acoustic microscopes consist of a transducer mounted on an acoustic focus lens. The transducer is excited with tone bursts and the acoustic energy is scanned over a sample that is held at the focus plane of the lens. The reflected energy is detected and the signal is amplitude detected and used as the z-modulation for an image displayed on a cathode-ray tube. The amplitude of the reflected signal is a function of the impedance of the sample at the location of the acoustic beam and its position with respect to the location of the focus of the lens. Thus, the image obtained indicates the changes in mechanical properties over the surface of the sample such as defects. U.S. Pat. No. 4,028,933 describes this type of acoustic microscope.

The use of acoustic waves to probe the interior of specimens is well known. A transducer applies acoustic waves at one surface of the sample which are picked up after transmission through or reflection from the sample by a suitable receiver mounted to receive acoustic waves at the opposite surface. Any flaw, inclusion or void in the interior of the sample results in a change in the transmitted or reflected energy. These changes are displayed on an oscilloscope or suitable display. The location of subsurface defects or inclusions is done by time-gating the application of energy and its reception to assure collection of acoustic waves generated at a given focal plane below the surface of the sample. In order to obtain information of defects or the like near the surface, the systems are usually operated with broad-band transducers and at high frequencies. Nevertheless, a "dead zone" is always present and no defects or inclusions can be detected in the near surface of the sample.

I have discovered that by detecting the spectral reflection from the surface, the mode converted Rayleigh waves and the reflection of acoustic energy reflected from an interior defect, inclusion or void, and combining these signals so that they interfere, it is possible to provide an output signal which shows enhanced response to near-surface inclusions, defects or voids.

It is an object of the present invention to provide an acoustic microscope for detection of near-surface defects and inclusions.

It is another object of the invention to provide an acoustic microscope for detection of near-surface defects and inclusions which is simple in construction and operation.

It is a further object of the present invention to provide an acoustic microscope which operates in a quasi-continuous wave mode whereby signals need not be time resolved.

It is still another object of the present invention to provide an acoustic microscope which makes use of interference between surface, Rayleigh waves and object plane waves to provide an enhanced signal.

The foregoing and other objections of the invention are achieved by an acoustic microscope in which a focusing transducer directs acoustic energy to a sample so that it is focused on a plane near the surface and the energy reflected from the plane, mode-converted and reflected waves are collected and interfere to produce an output signal.

These and other objects of the invention and the manner in which they are achieved will be more readily understood from the following description and accompanying drawings of which:

FIG. 1 shows a focused transducer serving as an acoustic wave transmitter and receiver focused at a near-surface plane of a specimen.

FIG. 2 shows the signals applied to and received from the transducer.

FIG. 3 is a block diagram of an acoustic microscope in accordance with the invention.

Referring to FIG. 1, a focused acoustic transducer 11 is shown connected to transmit or receive acoustic energy to and from a sample 13. The transducer is excited by electrical signals applied to lead 12. The transducer also serves to receive acoustic waves and provide electrical signal to the line 12. The transducer is located so that when the sample is brought within the focus distance of the transducer, as shown in FIG. 1, mode-converted (leaky) Rayleigh waves 14 are excited on the sample surface. As seen, these waves travel on the surface and return to the transducer within the critical angle. It is known in the field of acoustic microscopy that interference of the specularly reflected signal and the mode-converted Rayleigh waves is the main source of contrast in a typical acoustic microscope where the surface is analyzed. It has also been believed that no contribution is made from signal reflected from a focal plane which is within the sample. I have discovered that signal from the focal plane 16 of the transducer within the sample can be a major source of contrast and detail in an acoustic microscope picture. Thus, in accordance with the present invention, the focused transducer 11 is defocused from the surface or interface between the sample and water which conducts the acoustic waves from the transducer and is focused at the focal plane 16 within the sample.

In operation of the acoustic microscope in accordance with the invention, a long burst—10 to 15 cycles—of signal is used to excite the transducer 11, such as the signal shown at 18, FIG. 2. This signal strikes the sample and the contribution to the interface echo are the specular reflection from the surface and the mode-converted Rayleigh waves 14. Signal is also reflected from the focal plane 16 within the sample. These specular reflected, mode-converted and focal plane reflected waves are detected by the transducer. Since there is no time separation all of the signals are received at substantially the same time. The signals combine and interfere with each other to give rise to an interference signal whose amplitude changes in response to flaws, inclusions or voids at the focal plane 16.

Referring to FIG. 2, the output of the transducer when no subsurface defect, inclusion, or voids are present, is shown at 19. The output when such defects, inclusions or voids are present at the focal plane is of greater or smaller amplitude depending on whether we are getting constructive or destructive interference with the signal from the interface. An example of constructive interference between the interface signal and the defect signal is shown at 21.

A suitable drive and detection circuit is shown in FIG. 3 for use in exciting the transducer and processing signals from the transducer. The pulse generator 26 controls the waveform generator 27 which generates sine-wave burst 18. The waveform generator operates at 0.1–20 MHz. This is a low frequency for acoustic microscopes. The burst is amplified by amplifier 28, amplitude controlled by attentuator 29, and applied to the transducer 11 whereby to generate focused acoustic waves 30. The burst 18 is applied to protection circuit 31 which limits the amplitude of the waves reaching the detection and processing circuits to prevent saturation of the amplifier. The specularly reflected, mode-converted and focal plane acoustic waves are received by the transducer which generates an electrical output signal. The output signal is applied to the attenuator 32 via the protection circuit 31. The signal is amplified by amplifier 33 and detected by detector 34 which provides a signal representative of the received amplified signal. The output of the amplitude detector 34 is applied to a sample and hold circuit 36 which retains the amplitude of the signal until the signal is sampled by the output from the pulse generator 37 and applied to the scan control drive which drives the intensity control of the cathode-ray display. The mechanical scanner 38 scans the object in the x-y direction and signals therefrom are applied to the scan control which controls the cathode-ray tube scan whereby a point-by-point display is formed, one point for each burst 18 as the beam scans the tube. By appropriately adjusting the cathode-ray tube control, the display will show the defects at the near surface focal plane.

By adjusting the position of the transducer, the position of the focal plane is determined and therefore the depth of the subsurface defects, inclusions or voids. The display provides an indication of location and size of the defects, inclusions or voids.

Thus, there is provided an acoustic microscope which permits detection and location of near subsurface flaws, inclusions or voids in a solid sample.

What is claimed is:

1. The method of detecting and isolating near-surface flaws, inclusions or voids in a solid sample which comprises: directing a focused beam of acoustic energy at the sample with its focal plane at the subsurface flaw, inclusion or void location; scanning the sample with the beam; detecting acoustic energy specularly reflected and mode converted at the surface of the sample and acoustic energy reflected by subsurface flaws, inclusions or voids at the focal plane and generating an interference signal; and processing said signal and forming a signal indicative of the subsurface flaws, inclusions or voids.

2. The method as in claim 1 in which the processing includes detecting the amplitude of the interference signal.

3. The method as in claim 1 in which the beam is scanned by moving the sample.

4. The method as in claim 1 including the additional step of forming a display showing the subsurface flaws, inclusions or voids.

* * * * *

UNITED STATES PATENT AND TRADEMARK OFFICE
CERTIFICATE OF CORRECTION

PATENT NO. : 4,620,443
DATED : Nov 4, 1986
INVENTOR(S) : Butrus T. Khuri-Yakub

It is certified that error appears in the above—identified patent and that said Letters Patent is hereby corrected as shown below:

Column 1, after the title insert:

"This Invention was made with Government support under Contract No. W-7405-ENG-82 awarded under the Department of Energy. The Government has certain rights in this Invention."

Signed and Sealed this

Twentieth Day of October, 1987

Attest:

DONALD J. QUIGG

*Attesting Officer*  *Commissioner of Patents and Trademarks*